(12) United States Patent
Mallory (10) Patent No.: US 7,882,838 B2
(45) Date of Patent: Feb. 8, 2011

(54) EXOTHERMIC CONDOM PACKAGING

(75) Inventor: Kevin Mallory, Albuquerque, NM (US)

(73) Assignee: Blaise Harrison, LLC, Albuquerque, NM (US)

(*) Notice: Subject to any disclaimer, the term of this patent is extended or adjusted under 35 U.S.C. 154(b) by 304 days.

(21) Appl. No.: 12/041,469

(22) Filed: Mar. 3, 2008

(65) Prior Publication Data
US 2008/0210579 A1  Sep. 4, 2008

Related U.S. Application Data

(60) Provisional application No. 60/892,504, filed on Mar. 1, 2007.

(51) Int. Cl.
  *A61F 6/02* (2006.01)
(52) U.S. Cl. .................. 128/842; 128/844
(58) Field of Classification Search ........... 128/842, 128/844; 604/347–353
  See application file for complete search history.

(56) References Cited

U.S. PATENT DOCUMENTS

| | | |
|---|---|---|
| 3,240,396 A | 3/1966 | Friedenberg |
| 3,250,680 A | 5/1966 | Menkart et al. |
| 3,341,418 A | 9/1967 | Moses |
| 3,585,982 A | 6/1971 | Hollinshead |
| 3,638,786 A | 2/1972 | Borecki et al. |
| 3,744,625 A | 7/1973 | Chin |
| 3,866,800 A | 2/1975 | Schmitt |
| 3,878,118 A | 4/1975 | Watson |
| 3,983,994 A | 10/1976 | Wyslotsky |
| 4,439,416 A | 3/1984 | Cordon et al. |
| 5,208,031 A | 5/1993 | Kelly |
| 5,538,720 A | 7/1996 | Jendryssek-Pfaff et al. |
| 5,549,196 A | 8/1996 | Kassman |
| 5,638,949 A | 6/1997 | Jones |
| 5,862,908 A | 1/1999 | Arbin |
| 5,954,230 A | 9/1999 | Blette |
| 6,036,004 A | 3/2000 | Bowen |
| 6,076,661 A | 6/2000 | Abadi |
| 6,152,335 A | 11/2000 | Stern et al. |
| 6,428,791 B1 | 8/2002 | Lezdey et al. |
| 7,214,390 B2 | 5/2007 | Barone, Jr. et al. |
| 7,303,328 B2 | 12/2007 | Faraldi et al. |
| 7,392,807 B2* | 7/2008 | Osterberg ................ 128/830 |
| 2004/0004088 A1 | 1/2004 | Yerby et al. |
| 2005/0045497 A1 | 3/2005 | Sample |
| 2006/0188528 A1* | 8/2006 | Chuah et al. ............. 424/400 |
| 2007/0167776 A1* | 7/2007 | Kochavi et al. ........... 600/439 |
| 2007/0187429 A1 | 8/2007 | Farahmand |
| 2007/0253761 A1 | 11/2007 | May |
| 2008/0118417 A1 | 5/2008 | Mallory |

FOREIGN PATENT DOCUMENTS

| | | |
|---|---|---|
| JP | 10-085031 | 4/1998 |
| JP | 2005-231644 | 9/2005 |
| WO | WO-01-64176 | 9/2001 |

* cited by examiner

*Primary Examiner*—Michael A. Brown
(74) *Attorney, Agent, or Firm*—Deborah A. Peacock; Samantha A. Updegraff; Peacock Myers, P.C.

(57) ABSTRACT

Packaging for heating a condom using reactants that generate heat when they react with each other.

19 Claims, 5 Drawing Sheets

EXOTHERMIC CONDOM PACKAGING

CROSS-REFERENCE TO RELATED APPLICATIONS

This application claims priority to and the benefit of U.S. Provisional Patent Application Ser. No. 60/892,504, entitled "Exothermic Condom Packaging", to Mallory et al., filed on Mar. 1, 2007, and the specification thereof is incorporated herein by reference.

BACKGROUND OF THE INVENTION

1. Field of the Invention (Technical Field)

Embodiments of the present invention relate to exothermic condom packaging which releases heat through an exothermic chemical reaction of reactants that are preferably non-toxic and which most preferably comprise an aqueous solution, thus heating a condom contained in the packaging.

2. Description of Related Art

While condoms and their packaging have been known for some time, the known condoms and packaging that produce a warming sensation rely on sensation-producing chemicals, such as menthol, and thus do not produce a true warming effect. There is thus a need for a condom package which can quickly and effectively heat a condom prior to use thus providing a true warming effect.

BRIEF SUMMARY OF THE INVENTION

One embodiment of the present invention is a condom package comprising a plurality of chambers, a first reactant disposed in a first chamber, a second reactant disposed in a second chamber, at least one breachable seal between the chambers with the reactants and a condom disposed in one of the chambers. The reactants are reactable to produce an exothermic reaction when in contact after the seal is breached. The package can have the condom in contact with at least one of the reactants prior to breaching the seal. Alternatively, the condom does not have contact with the reactants prior to breaching the seal. In addition, the condom does not have to have contact with the reactants even after the seal is breached. If the condom does not have contact with the reactants after the seal is broken then the condom is preferably heated by thermal conduction through one or more walls of the plurality of chambers from the exothermic reaction of the reactants after the reactants are in contact with each other. The package can further comprise a flavoring agent and/or a lubricant disposed within at least one of the chambers.

Another embodiment of the present invention is a method for using an exothermic condom package. This method provides a package having a plurality of chambers, a first reactant disposed in the first chamber, a second reactant disposed in the second chamber, at least one breachable seal and a condom disposed in one of the chambers. Then at least one of the seals is breached which contacts and reacts the reactants with each other causing an exothermic reaction and generating heat. The condom is then heated from the exothermic reaction and the condom is then removed from the packaging for use. The method can have the condom contacting at least one of the reactants prior to breaching the seal. The method can optionally prevent the condom from having contact with the reactants prior to breaching the seal. Finally, the method can prevent the condom from having contact with the reactants after breaching the seal. If the condom does not have contact with the reactants after breaching the seal, the condom is heated by thermal conduction through one or more walls of the plurality of chambers after reacting the reactants and generating heat. The method can also have a flavoring agent and/or a lubricant in at least one of the chambers.

A further embodiment of the present invention is a method for heating a condom comprising mixing a plurality of reactants to produce an exothermic reaction, generating heat from the reaction and heating the condom. This method can additionally comprise storing the reactants and the condom within a package and optionally comprise contacting the reactants with one another at a time just prior to using the condom. The time can be less than about 10 minutes prior to using the condom. The reactants can be separated from the condom so there is no contact between the reactants and the condom, or at least one of the reactants can have contact with the condom.

Objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE SEVERAL VIEWS OF THE DRAWINGS

The accompanying drawings in the attachment, which are incorporated into and form a part of the specification, illustrate one or more embodiments of the present invention and, together with the description, serve to explain the principles of the invention. The drawings are only for the purpose of illustrating one or more preferred embodiments of the invention and are not to be construed as limiting the invention. In the drawings.

DETAILED DESCRIPTION OF THE INVENTION

An embodiment of the present invention relates to a condom package which heats a condom and contains a warming personal lubricant contained therein. Preferably, the condom is heated by an exothermic reaction which is most preferably initiated by a user breaking or breaching an inner seal that separates the reactants.

The term "reactant(s)", as used throughout the specification and claims, includes one or more chemicals or components which can be combined with one or more other chemicals or components to produce an exothermic reaction.

Figure 1:
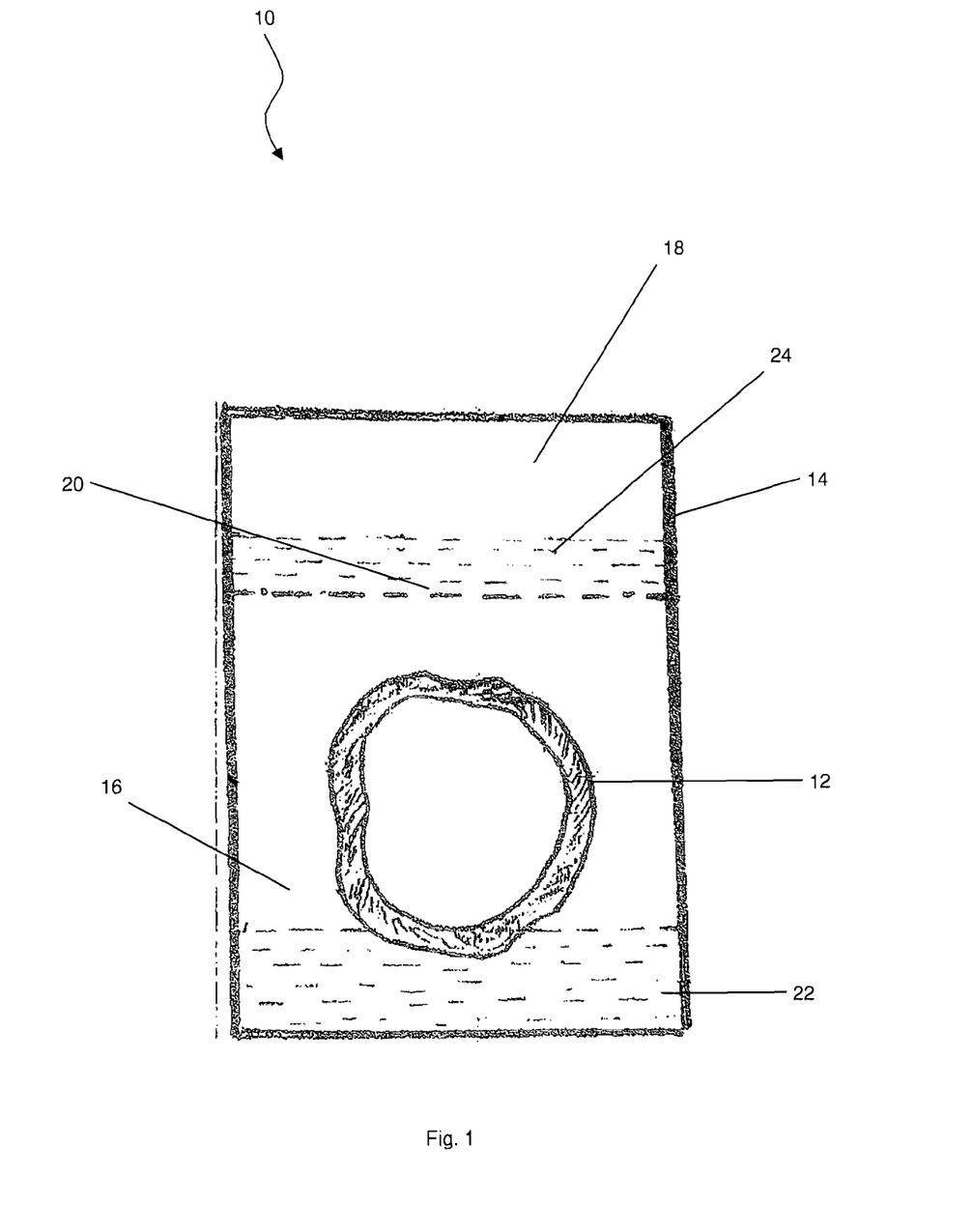
FIG. 1 illustrates an embodiment of the present invention wherein a condom is disposed within a substantially flat exothermic packaging and wherein the condom is disposed in communicable contact with at least one reactant.

As illustrated in the embodiment of FIG. 1, assembly 10 preferably comprises condom 12, which is preferably in a rolled or otherwise flattened condition, and package 14. Package 14 preferably comprises first chamber 16 and second chamber 18. Chambers 16 and 18 are preferably separated by seal 20. In the embodiment of FIG. 1, condom 12 is preferably contained within first chamber 16. First reactant 22 is preferably disposed within first chamber 16 of package 14, and second reactant 24 is preferably disposed within second chamber 18 of package 14. The packaging in FIG. 1 is substantially flat.

Figure 2:
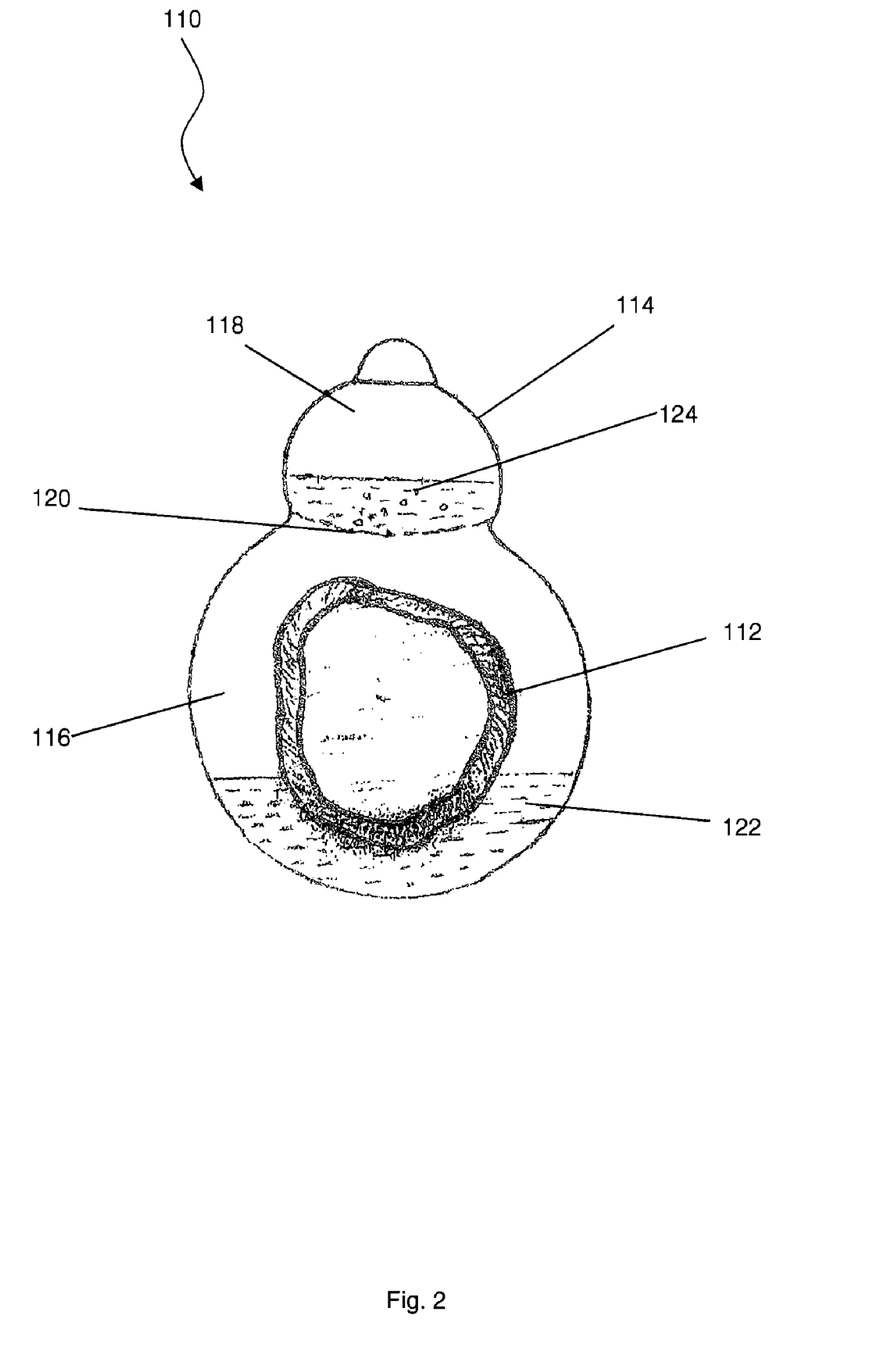
FIG. 2 illustrates an embodiment of the present invention wherein a condom is disposed within a substantially three-dimensional exothermic packaging and wherein the condom is disposed in communicable contact with at least one reactant.

As illustrated in the embodiment of FIG. 2, assembly 110 preferably comprises condom 112, which is preferably in a rolled or otherwise flattened condition, and package 114. Package 114 preferably comprises first chamber 116 and second chamber 118. Chambers 116 and 118 are preferably separated by seal 120. In the embodiment of FIG. 2, condom 112 is preferably contained within first chamber 116. First reactant 122 is preferably disposed within first chamber 116 of package 114, and second reactant 124 is preferably disposed within second chamber 118 of package 114. The packaging in FIG. 2 is substantially three-dimensional.

While numerous materials are known to those skilled in the art for providing packaging, the packaging preferably comprises a waterproof material and is preferably a plastic material, although any materials useful for containing a condom and reactants may be used in accordance with the invention. The seal is preferably the barrier formed between first and second chambers. The seal is most preferably formed by thermally fusing an upper-portion of the packaging to a lower-portion thereof. Although, adhesively bonding upper and lower-portions of the packaging can also provide desirable results, as well as other manners of providing the seal as known in the art.

One more lubricants and/or flavoring agents can also optionally be included within first chamber 216 and/or second chamber 218. Although second chamber 218 is most preferably an extension of first chamber 216, second chamber 218 can optionally comprise a second container or chamber disposed within first chamber 216 (see FIG. 3). In this embodiment, seal 220 thus comprises an outer portion or edge of second chamber 218.

Figure 3:
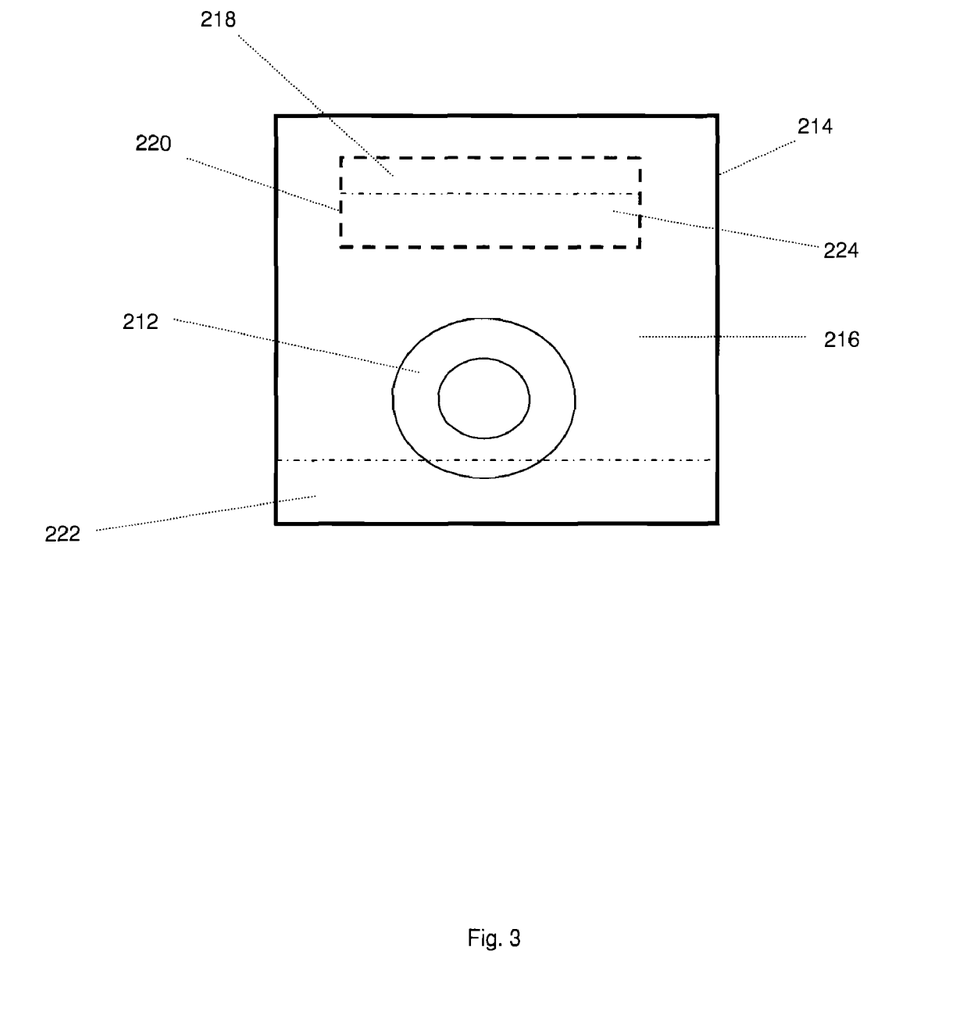
FIG. 3 illustrates an embodiment of the present invention wherein a condom is disposed within exothermic packaging and wherein a second chamber is disposed within a first chamber.

In using the embodiments of the present invention illustrated in FIGS. 1-3, a user preferably squeezes the first and/or second chambers or otherwise causes the seal to be breached, thus enabling the first reactant to be mixed with the second reactant, which thus heats the condom. After the condom is heated to a desired temperature, the user preferably cuts or otherwise tears open the packaging and removes the condom therefrom. In these embodiments, the condom is in contact with at least one reactant before the seal is breached.

While various manners of providing seals are known to those skilled in the art, the seals are preferably provided by attaching an upper-portion of the packaging to a lower-portion thereof, and most preferably by thermally fusing an upper-portion of the packaging to a lower-portion thereof. However, desirable results can also be obtained by adhesively adhering the upper-portion to the lower portion thereof.

In one embodiment, one or more lubricants and/or a flavoring agent can be disposed in one or more chambers. Although some of the embodiments of the present invention show first and second chambers comprising or containing reactants, other embodiments of the present invention can optionally provide multiple other chambers which can themselves optionally hold one or more other reactants or additives.

Figure 4:
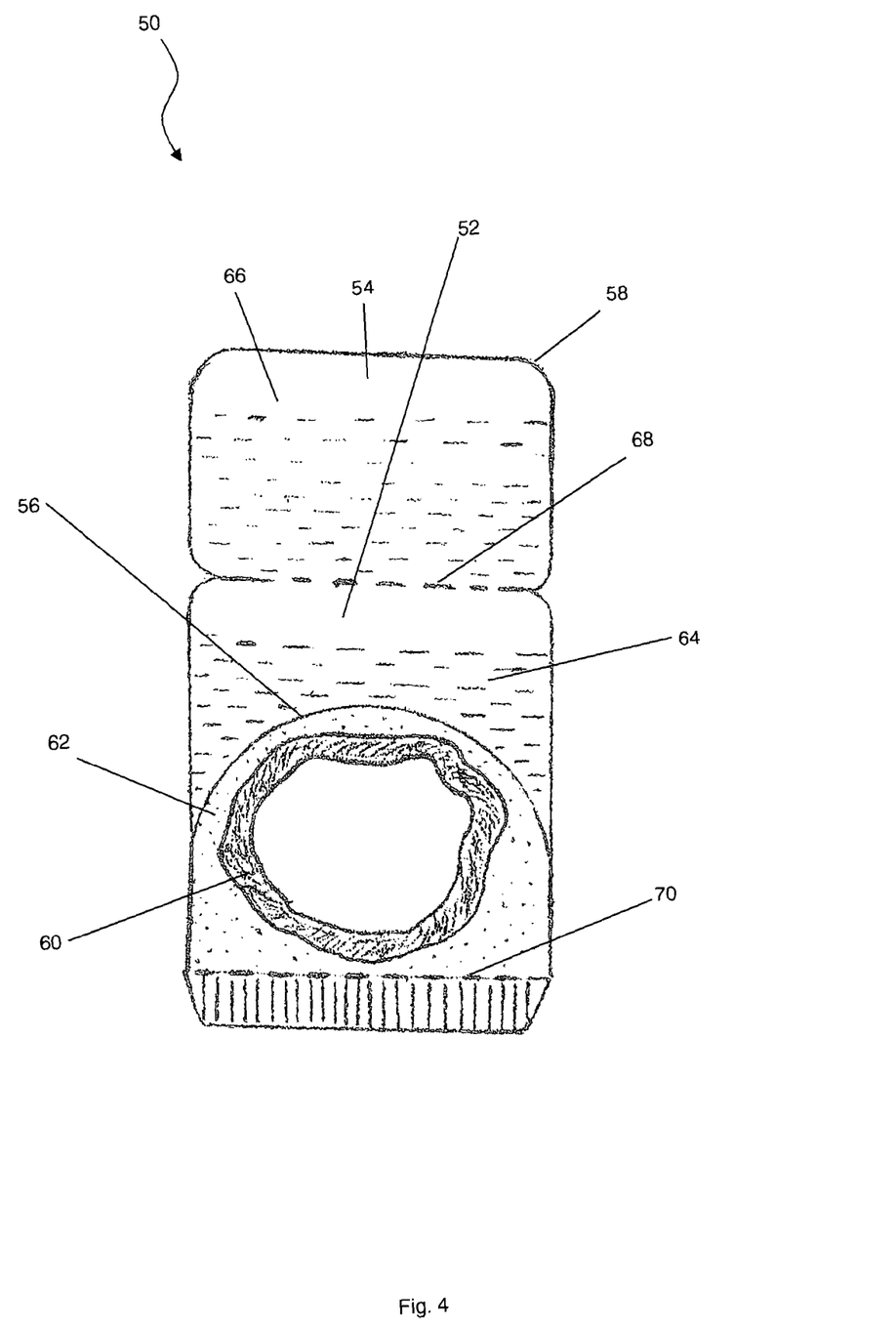
FIG. 4 illustrates an embodiment of the present invention wherein a condom is disposed within an exothermic packaging and wherein the condom is isolated from the reactants prior to and during the mixing thereof.

FIG. 4 illustrates an embodiment of the present invention wherein assembly 50 preferably comprises first chamber 52, second chamber 54 and third chamber 56 of packaging 58. Condom 60 is preferably, but optionally, disposed within third chamber 56 of packaging 58. A lubricant and/or flavoring agent 62 are also preferably disposed within third chamber 56. Third chamber 56 is preferably formed with a thermally conductive material such as foil, although other materials including but not limited to plastic, can produce desirable results as well. First chamber 52 of packaging 58 preferably houses first reactant 64. Second chamber 54 of packaging 58 preferably houses second reactant 66. Seal 68 preferably separates packaging 58 into first chamber 52 and second chamber 54. Seal 68 is preferably provided by attaching an upper-portion of packaging 58 to a lower-portion thereof, and most preferably by thermally fusing an upper-portion of packaging 58 to a lower-portion thereof. Of course, adhesively attaching upper and lower-portions of packaging 58 can also produce desirable results. Seal 70 is preferably attached near a terminal portion of packaging 58, such that condom 60 can be removed from third chamber 56. Seal 70 preferably comprises a tear-away or otherwise breakable seal, and is most preferably provided by thermally fusing an upper-portion of packaging 58 to a lower portion thereof. One or more perforations can optionally be disposed through or near seal 70 for ease in tearing or opening.

To use the embodiment illustrated in FIG. 4, a user preferably squeezes first chamber 52 and/or second chamber 54, or otherwise causes seal 68 to be breached, enabling first reactant 64 to mix with second reactant 66, thus resulting in an exothermic reaction which heats optional lubricant and/or flavoring agent 62 and condom 60 by thermal conduction through one or more walls of third chamber 56 and thereby heating condom 60 without direct contact to any of the reactants. After condom 60 is heated to a desired temperature, the user preferably tears or otherwise cuts open packaging 58 near or at seal 70 and removes condom 60 from packaging 58. As illustrated in FIG. 4, the condom does not have contact with the reactants even after the seals are breached.

Figure 5A:
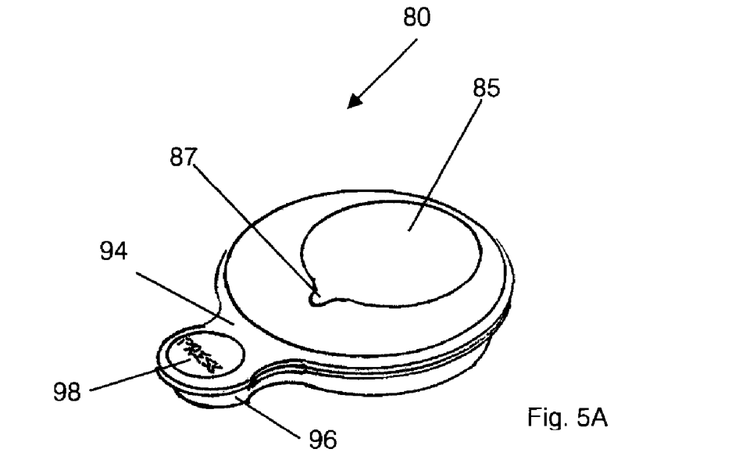
FIG. 5 illustrates an embodiment of the present invention wherein a condom is disposed within burstable packaging.
Figure 5B:
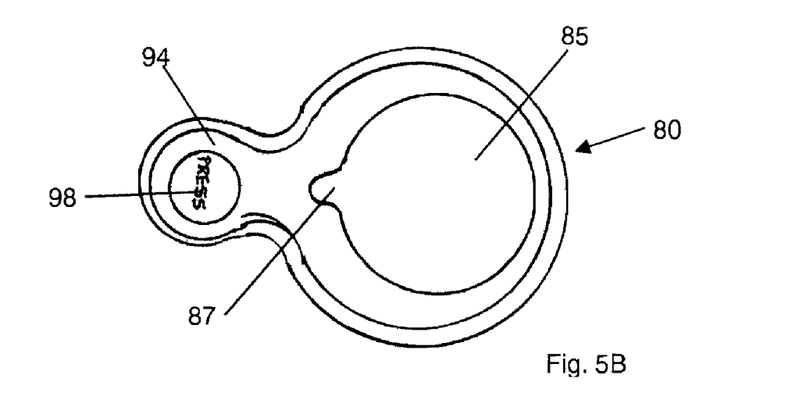
Figure 5C:
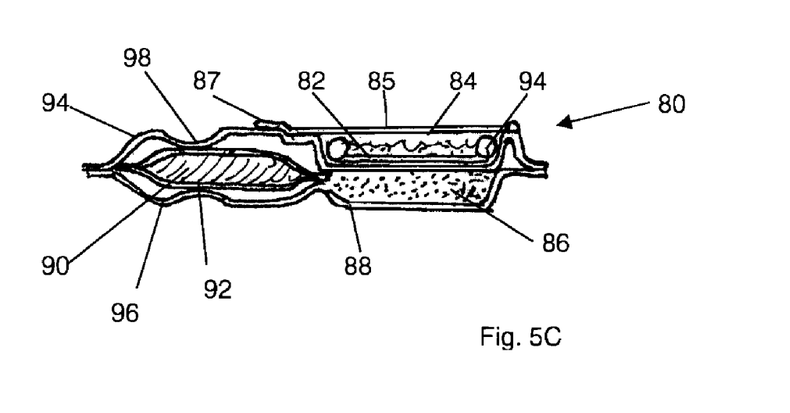

FIGS. 5A-C illustrate another embodiment of the present invention. As shown therein, assembly 80 preferably comprises condom 82 which is preferably rolled or otherwise flattened and disposed with chamber 84 of assembly 80. Optionally, lubricant 94, is also disposed near condom 82 in chamber 84. Lid 85 covers a top of chamber 84. Lid preferably comprises a pull tab 87. A reactant, preferably a powder reactant 86, is disposed in another chamber 88. Another reactant, preferably a liquid reactant 90, is disposed within another separate chamber 92. Chamber 88 is preferably disposed between top cover 94 and bottom cover 96. Chamber 88 is disposed near or partially within chamber 86 and these chambers 88 and 86 are sealed from each other, initially. Disposed in top cover 94 is an area or indentation 98 which is pressed by the user.

To use the embodiment illustrated in FIGS. 5A-C, the user presses on press area 98, which causes chamber 92 to compress and burst. Reactant or liquid 90 flows or reacts with reactant 86 in chamber 88 to create an exothermic reaction. When condom 82 is sufficiently heated, the user pulls on pull tab 87, lifting lid 85, to withdrawn condom 82 for use. In this embodiment, condom 82 is not in contact with reactants 86 and 90.

One embodiment of the present invention comprises contacting the reactants with one another at a time just prior to using the condom. Another embodiment of the present invention comprises contacting the reactants with one another at a time of less than about 10 minutes prior to using the condom.

A further embodiment of the present invention comprises not contacting the condom with the reactants at all and using thermal conduction to heat the condom.

Reactants useful in the present invention include but are not limited to the components described herein. Lubricants useful in the present invention include but are not limited to the components described herein. Flavoring agents useful in the present invention include but are not limited to synthetic or natural flavor blends available in the food and flavor industry, and includes the components described herein. A detailed discussion of reactants, lubricants and flavoring agents is discussed below.

Reactants

The exothermic reaction in this invention does not involve or require water from the human tissue as in other lubricants. Instead, the invention releases a controlled amount of water during the reaction. Thus, it is rendered safer then other warming products since neither the epidermis nor the mucosa acts as a partner or a vessel for the reaction. The liquid product of the reaction is warm, preferably approximately 5 to 30 degrees Fahrenheit above ambient temperature, and retains and gently radiates such temperature for about 5 to 25 minutes from the time of application. It is also formulated to the pH environment of healthy living tissue, such as the skin, the vaginal cavity or other mucosa, and is a mild, non-irritant on healthy normal skin and/or mucosa.

The structure of the media in which the warming reaction occurs is selected to accommodate and safely deliver a wide variety of natural and/or synthetic extracts and drugs known to help soothe some epidermal and vaginal symptoms, including but not limited to, dysmenorrhea.

The preferred reactants are compatible with spermicides including, but not limited to, certain Nonoxynol compounds and others such as methoxypolyoxyethyleneglycol 550 laurate.

The heat and warming effects of the reactants come from an acid-base (redox) exothermic reaction. The selection of an acid and/or a base depends on suitability and ability to instantly produce the desired heat as well as the nature of final reaction products and the safety impacts on the living tissue. Several preferred reactants are described below.

There are at least two reactants, described as Part A and Part B. Part A includes, but is not limited to, the reaction matrix as described above, plus the designated components (including but not limited to acid or combinations of acids) as selected for the heating reaction. Such acid(s) preferably include but are not limited to carboxylic, of the type mono-, di- or poly-carboxylic functional group(s) such as acetic, propionic, salicylic, valeric, vanillic, lactic, sorbic, glyceric, hippuric, benzoic, gluconic, malic, tartaric, glutaric, citric, and the like, but may also be of the amino carboxylic type, such as amino acetic acid (glycine), 2-amino glutaramic acid (glutamine), glutamic acid, folic acid, and the like. The monosodium salt of L-glutamic acid may also be used in the heat generating reaction due to its active carboxylic group. A suitable non-carboxylic acid, including but not limited to kojic acid or the like may be applied to Part A to enter the reaction as an acidulant or as a part of a buffer system.

Part B includes a reactant (preferably a base) that is completely or partially soluble in water, alcohol, ether and/or a mixture with or without the addition of one of the above mentioned polyols used herein as a thickener, solubilizer and/or aid for the heat transferring rate. The base reactant may include, but is not limited to, a hydroxide of one of the alkaline earth metal members of Ia and IIa of the periodic table, and/or the like reactants, preferably and including but not limited to potassium, sodium, magnesium, iron or calcium. Ammonium hydroxide (aqua ammonia) and/or ammonium bicarbonate and/or sodium carbonate or bicarbonate are preferable as they have been found to deliver the desired temperature using the proper molar ratio against the selected acid. The oxide salts of magnesium, calcium and sodium also were found to generate appreciable heat. Part B, in its composition, may or may not include certain amounts of viscosity builder, heat insulator, tissue rejuvenator, soothing agent and/or the dye as suitable. However, and in all cases, while selecting the proper reagents located in two separate reacting bodies, Parts A and B, they preferably exhibit one or more of the following attributes:

stability under normal conditions of temperature and pressure;

easy instant mix and easy application;

non-toxic, non-irritating reaction products to skin and/or mucosa;

heat stimulating and soothing effect;

easy to rinse or douche;

lubricating and moisturizing effect;

pH compatible with acceptable taste and/or aroma;

safe and feasible to deliver anti-inflammatory, antibiotic, spermicides, medicated oils, and botanical extracts;

environmentally friendly; and economical with reasonable shelf life.

The preferred reactants of the present invention are described below:

First Reactant. The water percentage preferably varies between approximately 20% to 90% by weight; and more preferably between approximately 65% and 75% by weight. Nonionic water soluble ether of cellulose and ethylene oxide (cellulose derived polymer) comprises a percentage between approximately 0.1% and 10% by weight and acts as a viscosity builder and thickening agent, by providing pseudoplasticity and regulating the rheology and water retention agent to provide high efficiency and solubility in a saline system, suspending and protecting colloidal action, binding and stabilizing. Part A also comprises mono-, di- and/or poly-saccharide in a percentage ranging from approximately 1% to 20% by weight, including, but not limited to, glucose or a glucose derivative, fructose, sucrose or a sucrose derivative, amylum, pectin, xanthan gum or derivative in a percentage ranging from approximately 0.1% to 5% by weight. Polyethylene glycol (PEG) series, such as PEG 300, is a Part A component in a percentage ranging from approximately 3% to 15% by weight. The polyol percentage, such as propylene glycol, is between approximately 1% to 35% by weight. The tissue rejuvenator, including but not limited to a polypeptide substance such as collagen and/or gelatin may be in the range of approximately 0.1 to 25% in some applications. One or more of the reactive acid's type and category is partially or completely dissolved in Part A in a percentage by weight ranging from approximately 2% to 60%, the list including, but not limited to:

Monocarboxylic type:

Acetic acid

Propionic acid

Salicylic acid n-Valeric acid

Vanillic acid

Glycine (amino acetic acid)

Lactic acid

Sorbic acid

Glyceric acid

Glutamine (2-amino-glutaramic acid)

Hippuric acid

Benzoic acid
Gluconic acid
Di-carboxylic type:
Malic acid
Folinic acid
Adipic acid
Tartaric acid (the D, L, DL and meso types)
Glutamic acid (amino acid)
Folic acid (amino acid)
Glutaric acid
Poly-carboxylic group acids
Citric acid
Non-carboxylic acid
Kojic acid (and the likes)

Natural flavors, when added, are preferably in the range of between approximately 0.01% and 5%.

Second Reactant. Part B comprises the base reactant which is one or a combination of the following ingredients supported by polyhydric alcohol and/or a suitable polyol as described above. The base reactant is partially or completely introduced as a solution or a paste. The base reactant is in the range of approximately 2% to 60% by weight and the amount added in this part is calculated to be in the proper ratio against the acid or combination of acids applied in Part A. Such ratio is drawn from the reaction equation(s) and calculated so that it allows the proper amount of positively charged protons or radicals to deliver the pH range desired and suitable for the application. A pH chart for certain example acids and a temperature table are illustrative. The base reactants include, but are not limited to, the following components: ammonium, sodium, potassium, magnesium, iron and/or calcium hydroxides. The carbonate and/or bicarbonate salts of sodium and/or ammonium and oxide salts of sodium, magnesium and calcium may also be added to Part B as sole salts or in combination with the hydroxide and/or the carbonates. Part B in its composition may or may not include certain amounts of viscosity builders, heat insulator, tissue rejuvenator, soothing agent and/or the dye as suitable. Part A or Part B my comprise a powder.

Flavoring Agents

Flavoring agents include, but are not limited to, aloe vera and derivatives and/or natural fruit essential oils and/or extracts, including but not limited to cucumber, vanilla, strawberry, lemon, lime, cherry, black raspberry, orange, citrus, mango, pineapple, blueberry, licorice, cinnamon, peppermint and rose oil. A sole ingredient and/or a mixture may be used as needed.

Lubricants

Lubricants may include anesthetics, including but not limited to benzocaine, lidocaine, benzyle alcohol, and the like. The inclusion of plant extracts, including but not limited to aloe vera extract, witch hazel, and the like, is also useful in achieving a soothing effect. Also suitable are certain soothing vegetable oils, including but not limited to olive, grape seed and jojoba oils.

Although the invention has been described in detail with particular reference to these preferred embodiments, other embodiments can achieve the same results. Variations and modifications of the present invention will be obvious to those skilled in the art and it is intended to cover all such modifications and equivalents. The entire disclosures of all references, applications, patents, and publications cited above and/or in the attachments, and of the corresponding application(s), are hereby incorporated by reference. The reactants, flavoring, materials, components, etc., set forth in U.S. patent application Ser. No. 11/875,667, entitled "Exothermic Personal Lubricant" are optionally, but not necessarily, used in one or more of the various embodiments set forth herein.

What is claimed is:

1. A condom package comprising:
    a plurality of chambers;
    a first reactant disposed in a first said chamber;
    a second reactant disposed in a second said chamber;
    at least one breachable seal between said chambers comprising said reactants;
    said reactants reactable to produce an exothermic reaction when in contact after said seal is breached; and
    a condom disposed in one of said chambers.

2. The package of claim 1 wherein said condom is in contact with at least one of said reactants prior to breaching said seal.

3. The package of claim 1 wherein said condom does not have contact with said reactants prior to breaching said seal.

4. The package of claim 1 wherein said condom does not have contact with said reactants after breaching said seal.

5. The package of claim 4 wherein said condom is heated by thermal conduction through one or more walls of said plurality of chambers from an exothermic reaction of said reactants after said reactants are in contact with each other.

6. The package of claim 1 further comprising a flavoring agent disposed within at least one said chamber.

7. The package of claim 1 further comprising a lubricant disposed within at least one said chamber.

8. A method for using an exothermic condom package comprising:
    providing a package having a plurality of chambers, a first reactant disposed in the first chamber, a second reactant disposed in the second chamber, at least one breachable seal and a condom disposed in one of the chambers;
    breaching at least one seal;
    contacting and reacting the reactants with each other causing an exothermic reaction and generating heat;
    heating the condom from the exothermic reaction; and
    removing the condom from the packaging for use.

9. The method of claim 8 further comprising contacting the condom with at least one of the reactants prior to breaching the seal.

10. The method of claim 8 further comprising preventing the condom from having contact with the reactants prior to breaching the seal.

11. The method of claim 8 further comprising preventing the condom from having contact with the reactants after breaching the seal.

12. The method of claim 11 further comprising heating the condom by thermal conduction through one or more walls of the plurality of chambers after reacting the reactants and generating heat.

13. The method of claim 8 wherein at least one of the chambers comprises a flavoring agent.

14. The method of claim 8 wherein at least one of the chambers comprises a lubricant.

15. A method for heating a condom comprising:
    providing a package comprising a condom and a plurality of reactants, the plurality of reactants disposed separately;
    mixing the plurality of reactants to produce an exothermic reaction; and
    generating heat from the reaction and heating the condom.

16. The method of claim 15 further comprising contacting the reactants with one another at a time just prior to using the condom.

17. The method of claim 16 comprising contacting the reactants with one another at a time of less than about 10 minutes prior to using the condom.

18. The method of claim 15 comprising not contacting the condom with the reactants.

19. The method of claim 15 further comprising contacting at least one of the reactants with the condom.

* * * * *